United States Patent
Walsh (10) Patent No.: US 9,770,341 B1
(45) Date of Patent: *Sep. 26, 2017

(54) MAGNETIC SPINAL IMPLANT

(71) Applicant: NuVasive, Inc., San Diego, CA (US)

(72) Inventor: Christopher Walsh, Parkland, FL (US)

(73) Assignee: NuVasive, Inc., San Diego, CA (US)

( * ) Notice: Subject to any disclaimer, the term of this patent is extended or adjusted under 35 U.S.C. 154(b) by 708 days.

This patent is subject to a terminal disclaimer.

(21) Appl. No.: 13/874,274

(22) Filed: Apr. 30, 2013

Related U.S. Application Data (60) Provisional application No. 61/640,378, filed on Apr. 30, 2012.

(51) Int. Cl.
*A61F 2/44* (2006.01)

(52) U.S. Cl.
CPC ............ *A61F 2/4455* (2013.01); *A61F 2/447* (2013.01); *A61F 2/4465* (2013.01); *A61F 2002/448* (2013.01); *A61F 2002/4475* (2013.01)

(58) Field of Classification Search
CPC .......... A61F 2/44; A61F 2/4455; A61F 2/446; A61F 2/4465; A61F 2/447; A61F 2002/4475; A61F 2002/448; A61F 2002/4485
USPC ........................................... 623/17.11–17.16
See application file for complete search history.

(56) References Cited

U.S. PATENT DOCUMENTS

| | | | | |
|---|---|---|---|---|
| 5,192,327 | A | * | 3/1993 | Brantigan ................. A61F 2/44 606/247 |
| 5,522,899 | A | * | 6/1996 | Michelson .......... A61F 2/30744 606/279 |
| 6,110,210 | A | * | 8/2000 | Norton .................... A61F 2/441 623/17.11 |
| 2002/0161443 | A1 | * | 10/2002 | Michelson ............ A61F 2/4455 623/17.11 |
| 2002/0183761 | A1 | * | 12/2002 | Johnson ............... A61B 17/025 606/90 |
| 2006/0015184 | A1 | * | 1/2006 | Winterbottom ........... A61F 2/44 623/18.11 |
| 2006/0189999 | A1 | * | 8/2006 | Zwirkoski ............... A61F 2/442 606/90 |
| 2007/0050030 | A1 | * | 3/2007 | Kim ................... A61B 17/7059 623/17.11 |
| 2007/0179493 | A1 | * | 8/2007 | Kim ................... A61B 17/7062 606/33 |
| 2008/0249622 | A1 | * | 10/2008 | Gray .................... A61F 2/4455 606/86 A |
| 2010/0023128 | A1 | * | 1/2010 | Malberg ................. A61F 2/442 623/17.16 |
| 2011/0257749 | A1 | * | 10/2011 | Fleischmann ............ A61F 2/38 623/17.16 |

(Continued)

*Primary Examiner* — Eric S Gibson
(74) *Attorney, Agent, or Firm* — Rory Schermerhorn; Jennifer Russell; NuVasive, Inc.

(57) ABSTRACT

The present invention provides for an improved spinal implant which is useful in bone fixation surgeries. The spinal implant as described herein provides a surgeon with a device that can easily and safely be inserted into the space previously occupied by the spinal disc. The spinal implant contains one or more magnets positioned on or within the device to self-align with one or more additional spinal implants inserted therein for the purpose of preventing misalignment of a plurality of implant devices during surgical procedures and preventing implant expulsion.

15 Claims, 8 Drawing Sheets

(56) References Cited

U.S. PATENT DOCUMENTS

| | | | | |
|---|---|---|---|---|
| 2013/0018467 A1* | 1/2013 | Suh | ............................ | A61F 2/44 623/17.16 |
| 2013/0150970 A1* | 6/2013 | Thaiyananthan | ........ | A61F 2/442 623/17.16 |
| 2013/0184823 A1* | 7/2013 | Malberg | ................... | A61F 2/442 623/17.13 |
| 2014/0058513 A1* | 2/2014 | Gahman | ................. | A61F 2/442 623/17.16 |

* cited by examiner

MAGNETIC SPINAL IMPLANT

FIELD OF THE INVENTION

The present invention relates to surgical implant devices useful for stabilization of adjacent bony structures of the spine, and more particularly to self aligning spinal implants for aligning two or more spinal implant devices used during bone fusion/fixation procedures.

BACKGROUND OF THE INVENTION

The central nervous system is a vital part of the human physiology that coordinates human activity. It is primarily made up of the brain and the spinal chord. The spinal chord is made up of a bundle of nerve tissue which originates in the brain and branches out to various parts of the body, acting as a conduit to communicate neuronal signals from the brain to the rest of the body, including motor control and sensations. Protecting the spinal chord is the spinal, or vertebral, column. Anatomically, the spinal column is made up of several regions, including the cervical, thoracic, lumbar and sacral regions. The cervical spine is made up of seven vertebrae and functions to support the weight of the head. The thoracic spine is made up of 12 vertebrae and functions to protect the organs located within the chest. Five vertebrae make up the lumbar spine. The lumbar spine contains the largest vertebra and functions as the main weight bearing portion of the spine. Located at the base of the spine is the five fused vertebrae known as the sacrum. The coccyx sits at the base of the spinal column and consists of four fused vertebrae.

Each of the vertebrae associated with the various spinal chord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal chords, it is not uncommon for individuals to suffer some type of spinal ailment, including spondylolisthesis, scoliosis, or spinal fractures, which are so severe as to require surgical intervention. One of the more common disorders associated with the spinal chord which requires surgical intervention is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. A disc herniation may compress the spinal cord and/or nerve roots and cause pain, loss of function, and even complete paralysis of the legs with loss of bowel and bladder control.

For most patients, rest and administration of pain and anti-inflammatory medications alleviates the problem. In severe cases, cases which have developed into spinal instability or severe disc degeneration, the damaged disc material between the vertebral bodies is removed and replaced with spinal stabilization implants. Restoration to the normal height allows the pressure on the nerve roots to be relieved. However, removal of the offending discal tissue has proven both difficult and quite dangerous. When the discs of the thoracic spine are approached posteriorly (from behind), the spinal cord is in the way. To approach the same herniation anteriorly (from the front) requires the very formidable procedure of thoracotomy (cutting open the chest) and moving the heart and lungs out of the way.

There are many different approaches taken to alleviate or minimize severe spinal disorders. One surgical procedure commonly used is a spinal fusion technique. Several surgical approaches have been developed over the years, and include the Posterior Lumbar Fusion (PLIF) procedure which utilizes a posterior approach to access the patient's vertebrae or disc space, the Transforaminal Lumbar Fusion (TLIF) procedure which utilizes a posterior and lateral approach to access the patient's vertebrae or disc space, and the Anterior Lumbar Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts. The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal implants and/or bone grafts have been inserted, a surgeon places the pedicle screws into a portion of the spinal vertebrae and attaches either rods or plates to the screws as a means for stabilization while the bones fuse.

While bone fusion technique often alleviates the pain associated with such disease, implantation of the spinal implant devices can be difficult. Gripping features, as well as various shapes, have been incorporated into the design of implants for ease of insertion and better hold on the vertebral endplates. Implantation is more difficult when the surgeon utilizes multiple implant devices, as proper alignment of the multiple implant devices can be very challenging. Implanting several implant devices can be time consuming, increasing the risk of surgical complications. Once implanted, the implant devices do not always remain at the site of implantation. Implant expulsion results from implants migrating and expelling out of the disc space, usually through the insertion pathway. Implants that migrate to the spinal chord or nerve roots can cause serious complications to the patient. While threaded features or teeth are used to prevent such migration, care must be used when incorporating these features into the design of the implant, as such features can result in localized stress risers in the end plates causing implant subsidence.

There exists, therefore, a need for an improved spinal implant that is easy to insert, is self-aligning when multiple spinal implants are used in a surgical procedure, and reduces the risk of spinal implant expulsion.

SUMMARY OF THE INVENTION

The present invention provides for an improved spinal implant which is useful in bone fusion/fixation surgeries. The spinal implant, as described herein, provides a surgeon with a device that can easily and safely be inserted into the space previously occupied by the spinal disc. The spinal implant contains one or more magnets positioned on and/or within the device to self-align with one or more additional spinal implants inserted therein for the purpose of preventing misalignment of a plurality of implant devices during surgical procedures. Additionally, the magnets prevent or minimize the possibility of implant expulsion or migration, particularly for multiple implants that are inserted between vertebrae endplates having non-uniform or uneven surfaces.

Accordingly, it is an objective of the present invention to provide an improved spinal implant device which is useful in bone fusion/fixation surgeries.

It is a further objective of the present invention to provide an improved spinal implant device used for Posterior Lumbar Fusion (PLIF) procedures.

It is yet another objective of the present invention to provide an improved spinal implant device used for Transforaminal Lumbar Fusion (TLIF) procedures.

It is a still further objective of the present invention to provide a self aligning spinal implant device which is useful in bone fusion/fixation surgeries.

It is a further objective of the present invention to provide a self centering spinal implant device which is useful in bone fusion/fixation surgeries.

It is yet another objective of the present invention to provide an improved spinal implant device comprising one or more magnets arranged to provide self-alignment with like configured spinal implant devices.

It is a further objective of the present invention to provide an improved spinal implant device comprising one or more magnets arranged to prevent or reduce implant expulsion or migration.

Other objectives band advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-6, an illustrative embodiment of the spinal implant in accordance with the present invention is shown. The spinal implant 10 is preferably suited for placement between adjacent human vertebral bodies. The implant 10 may be used in procedures such as Posterior Lumbar Fusion (PLIF) or Transforaminal Lumbar Fusion (TLIF). The spinal implant 10 contains a body 12 having a top surface 14, a bottom surface 16, opposing lateral sides 18 and 20, and opposing anterior 22 and posterior 24 portions. Each of the top surface 14 and the bottom surface 16 may contain ridges or teeth (not shown) to aid in implant stability. The device 10 is preferably made of a durable material, such as stainless steel, stainless steel alloy, titanium, aluminum, an alloy, carbon fiber composite, or other durable materials such as but not limited to polymeric, ceramic, and composite materials. For example, certain embodiments of the present invention may be comprised of a biocompatible, polymeric matrix reinforced with bioactive fillers, fibers, or both. Certain embodiments of the present invention may be comprised of a high-performance engineering thermoplastic such as polyetherether-ketone (PEEK) or other polymers such as polyvinyl chloride (PVC), polyethylene, polyesters of various sorts, polycarbonate, Teflon coated metal or ultra high molecular weight polyethylene (UHMWPE). Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally used due to their strength and biocompatibility.

Figure 1:
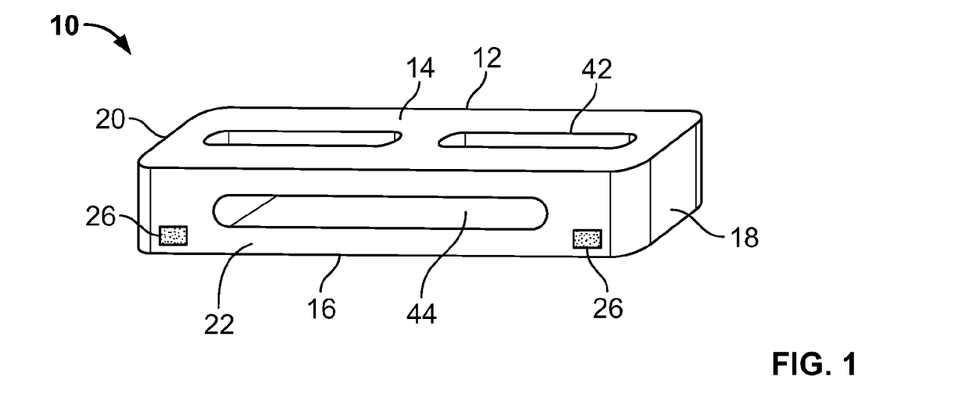
FIG. 1 is a front side perspective view of an illustrative embodiment of the spinal implant in accordance with the present invention.
Figure 2:
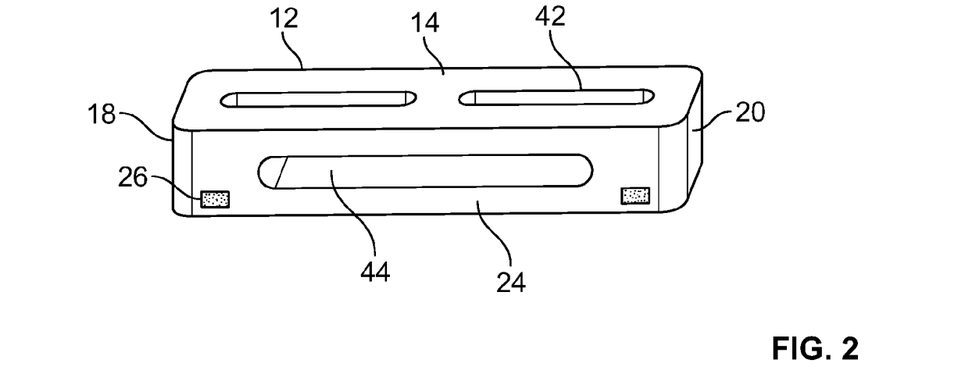
FIG. 2 is a back side perspective view of the illustrative embodiment of the spinal implant illustrated in FIG. 1.
Figure 3:
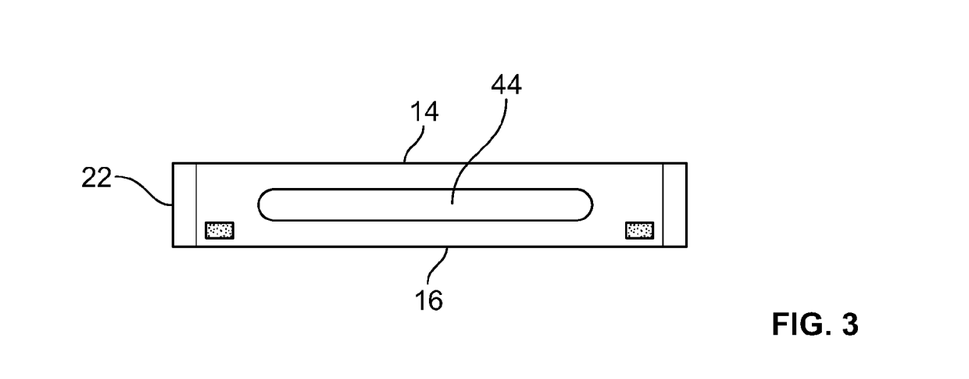
FIG. 3 is a side view of the illustrative embodiment of the spinal implant illustrated in FIG. 1.
Figure 4:
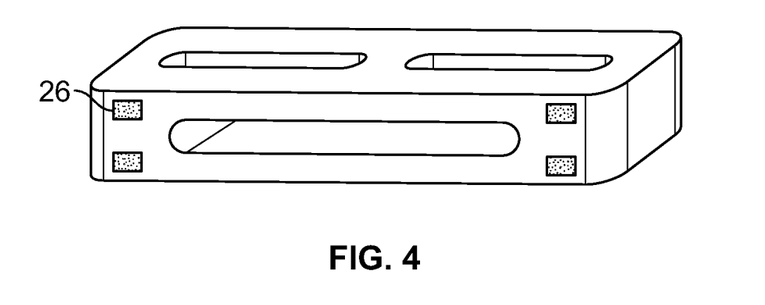
FIG. 4 is a perspective view of an alternative embodiment of the spinal implant in accordance with the present invention.
Figure 5:
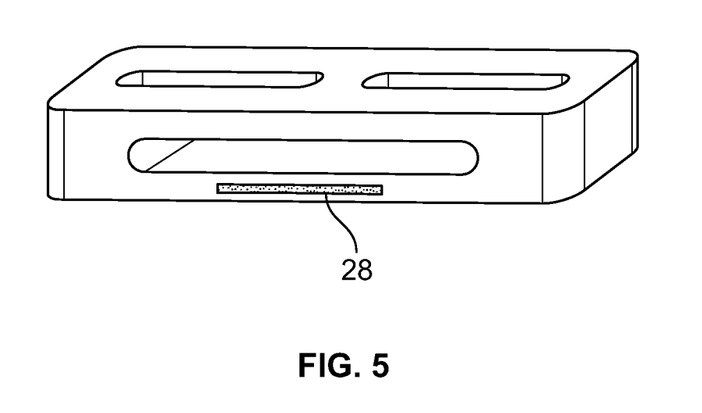
FIG. 5 is a perspective view of an alternative embodiment of the spinal implant in accordance with the present invention.

The body 12 of the spinal implant 10 contains one or more magnets 26 imbedded into the implant. The magnets 26 may be arranged to be an integral part of the outer surface of the top surface 14, the bottom surface 16, the opposing lateral sides 18 and 20, and the opposing anterior 22 and posterior 24 portions, or combinations thereof. As illustrated in FIGS. 1 and 2, magnets 26 are located at opposing ends of the anterior 22 (FIG. 1) and posterior potion 24 (FIG. 2). FIG. 4 illustrates an alternative embodiment of the spinal implant 10 which contains a pair of magnets 26 located at one end of the anterior portion 22 and a pair of magnets along the opposing ends of the anterior portion 22. Referring to FIG. 5, individual magnets 26 are replaced by a magnetic bar 28.

Magnets 26 or magnetic bar 28 may be permanent magnets, temporary magnets, or electromagnets, and can be made from any material that produces a magnetic field and is insertable into a human which does not result in a biological or an immune reaction or that does not pose safety risks to the individual. Other forms of the magnet may be use; for example, a magnetic powder or nano-magnetic particles can be applied to one or more portions of the main body 14 or be incorporated within the material that comprises the body 12.

Figure 6:
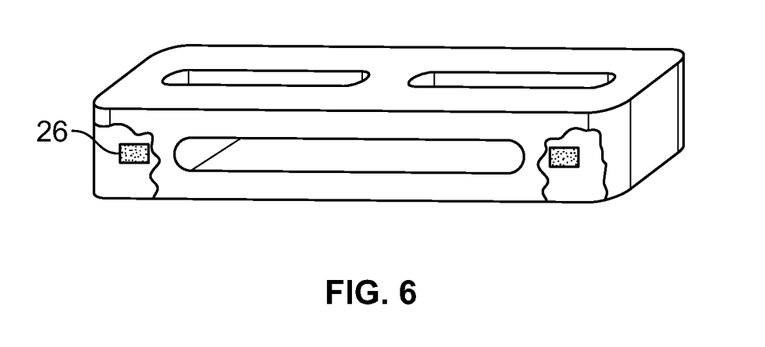
FIG. 6 is a perspective view of an alternative embodiment of the spinal implant in accordance with the present invention.

FIG. 6 illustrates an alternative embodiment of the spinal implant 10. In this embodiment, the magnet 26 or magnetic bar 28 (not illustrated) is integrally formed with the material that makes up the body 12. While the embodiments shown in FIGS. 1-6 illustrate the placement of the magnetic materials, either the magnets 26 or the magnetic bar 28, shown being placed along the anterior portion 22 or the posterior portion 24, or within the main body 12, such magnetic material can be placed anywhere along or within the top surface 14, the bottom surface 16, the opposing lateral sides 18 and 20, or combinations thereof.

Figure 10:
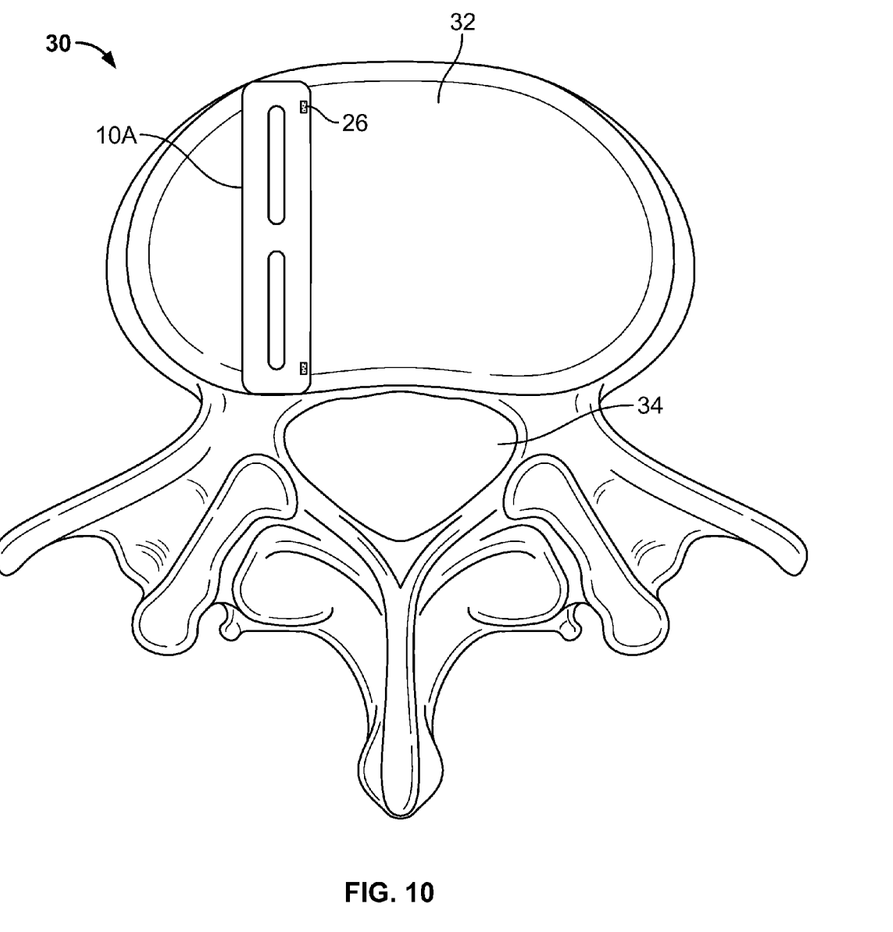
FIG. 10 illustrates implantation of a first spinal implant in accordance with the present invention within the disc space of adjacent vertebrae, resting on endplate.

Regardless of the positioning within or on the body 12, the magnets 26 or magnetic rod 28 provide a self-aligning function when two or more spinal implants 10 are aligned or placed at a proper distance so that the two or more spinal implants 10 are magnetically affected or drawn towards each other. Referring to FIG. 10, a top view of a vertebra 30 with an inserted first spinal implant 10A is illustrated. As shown, the vertebral disc has been removed to expose the vertebral endplate 32. The spinal chord, not illustrated, runs through the spinal canal 34. A single spinal implant 10 is shown inserted in between opposing endplates, not shown, and resting on endplate 32. Use of implants having magnets overcomes some of the problems associated with implanting multiple implants. For example, when an individual undergoes removal of the disc, it is a common procedure for the surgeon to prepare the endplate for insertion therein. Part of the preparation includes scraping of the endplate to provide a smooth surface for the implant to rest upon. However, the surface of the endplate is not always uniform, even with surgical preparation intervention. This presents a problem for insertion of multiple implants where the first implant is tightly secured between adjacent endplates but a remote portion of the endplate or an adjacent second endplate does not provide such a tight fit for the second implant because of the non-uniform nature of the endplate surface. The second implant is subject to floating, in which the second implant may move from its original implant site, risking sliding into the spinal canal or nerve roots, subjecting the patient to increased risk of serious damage.

Figure 11:
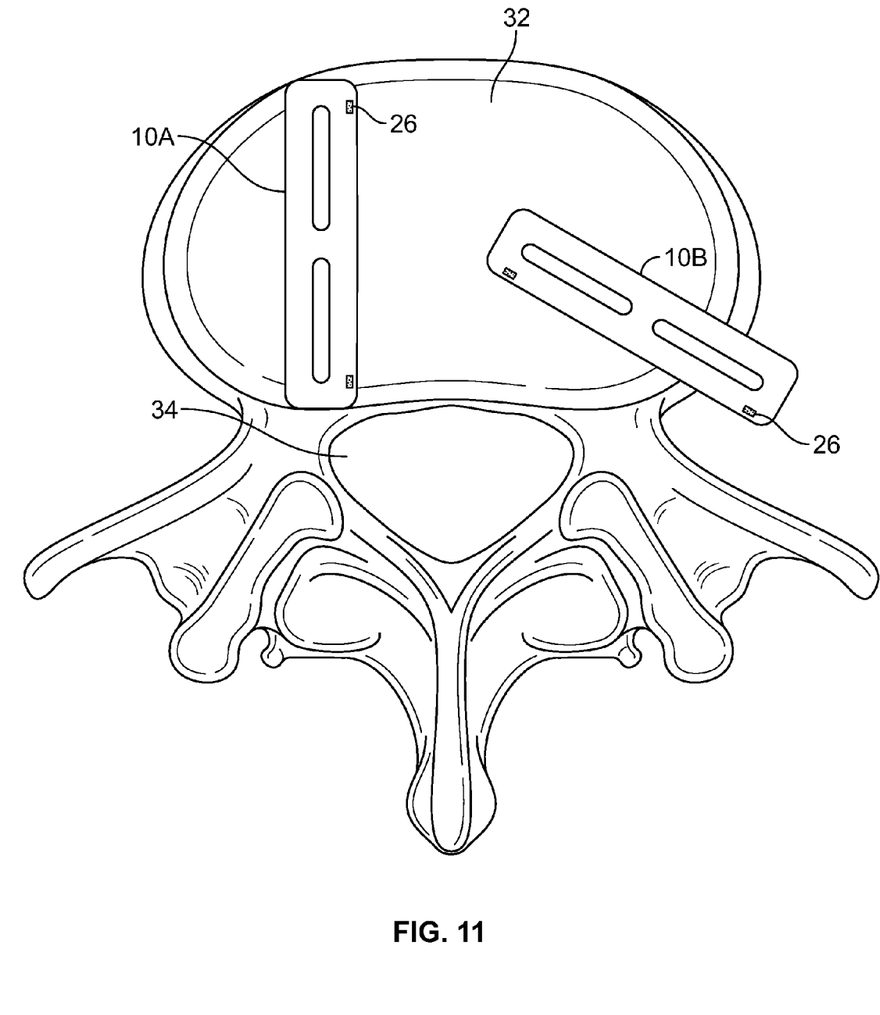
FIG. 11 illustrates implantation of a second spinal implant in accordance with the present invention within the disc space of adjacent vertebrae.
Figure 12:
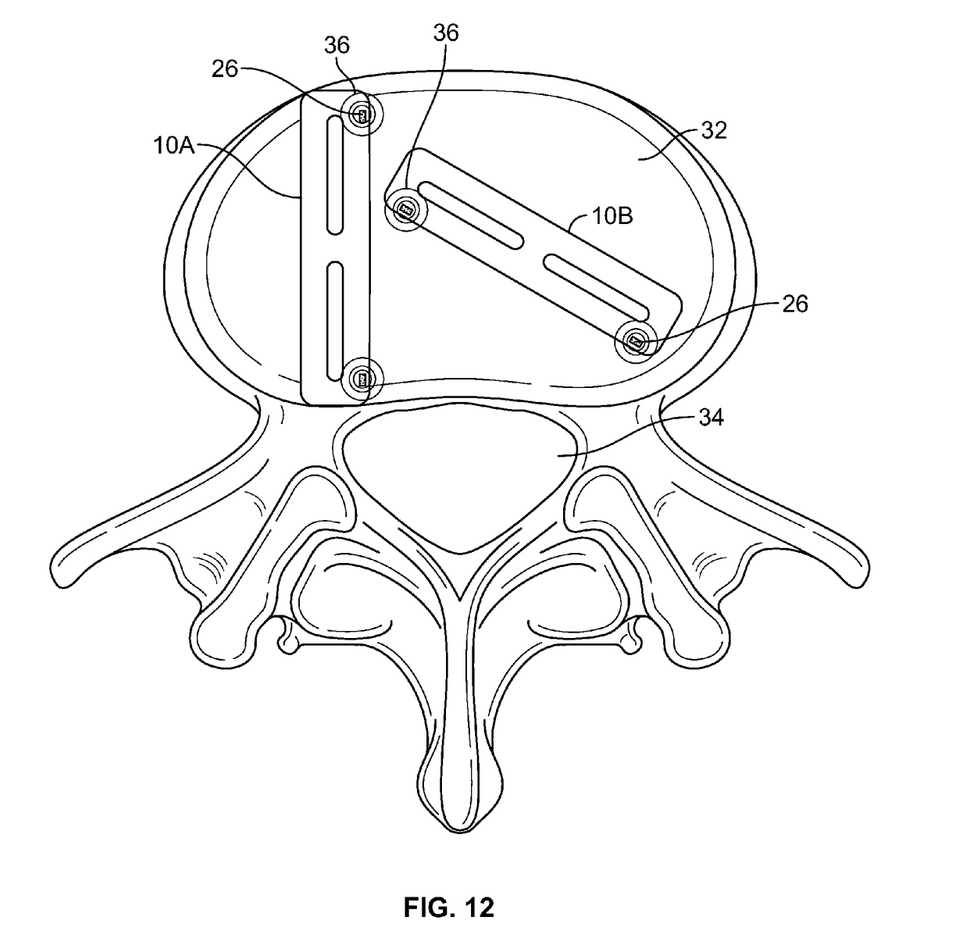
FIG. 12 illustrates the second spinal implant in accordance with the present invention further being moved into close proximity with the first spinal implant.

In bone fusion surgeries not using the spinal implant 10 in accordance with the present invention, inserting a second implant and aligning with a first spinal implant requires manipulation; there is no guarantee that correct alignment can be accomplished. However, using an implant in accordance with the present invention, self-alignment and self-centering can be accomplished. Referring to FIG. 11, as the second spinal implant 10B is inserted in between adjacent vertebrae, the surgeon is required to manipulate the spinal implant 10B until it is in close proximity to be affected by the magnetic fields 36 of the magnets 26 of spinal implant 10A, see FIG. 12. Once in close proximity, the magnetic field 36 of the second spinal implant 10B is drawn to the magnetic field 36 of the first spinal implant 10A.

Figure 13:
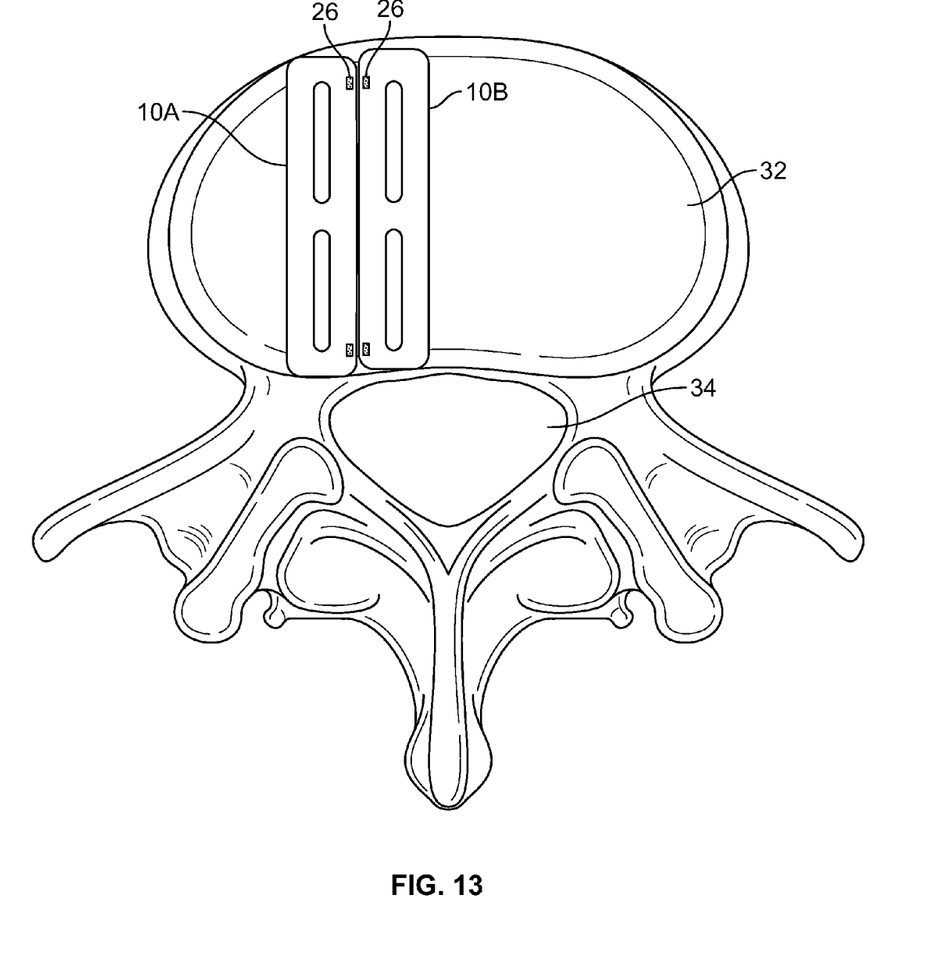
FIG. 13 illustrates the first and second spinal implant in a self-aligning arrangement.
Figure 14:
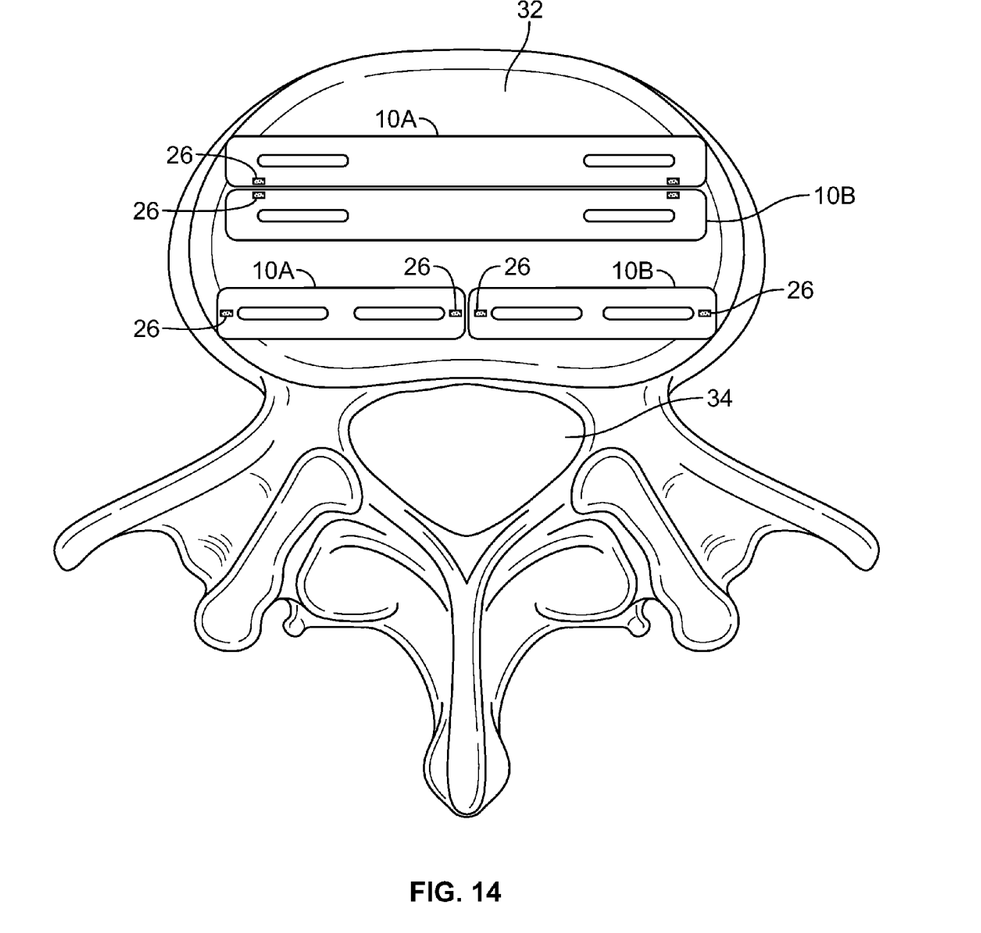
FIG. 14 illustrates the first and second spinal implant arranged in a different orientation within the within the disc space of adjacent vertebrae.

Accordingly, the magnets 26 cause the second spinal implant 10B to self align and self center with the first spinal implant 10A, see FIG. 13. In order to achieve the self-aligning and self-centering function, it is critical that the polarity of the magnets 26 on the spinal implant 10A are arranged so as to respond to the magnetic field produced by the magnets 26 of the spinal implants 10B. The two spinal implants 10A and 10B are aligned along their anterior 22 and posterior 24 sides, but could be arranged so that opposing sides 18 and 20, or the top surface 14 and bottom surfaces 16 align. This capability allows the spinal implants 10A and 10B to be arranged in different orientations, such as vertical alignment across the endplates arranged side to side or end to end, see FIG. 14, as opposed to horizontally aligned across the endplates. In any orientation, the spinal implants 10A and 10B self-align. While not illustrated, additional spinal implants may be inserted.

Figure 7:
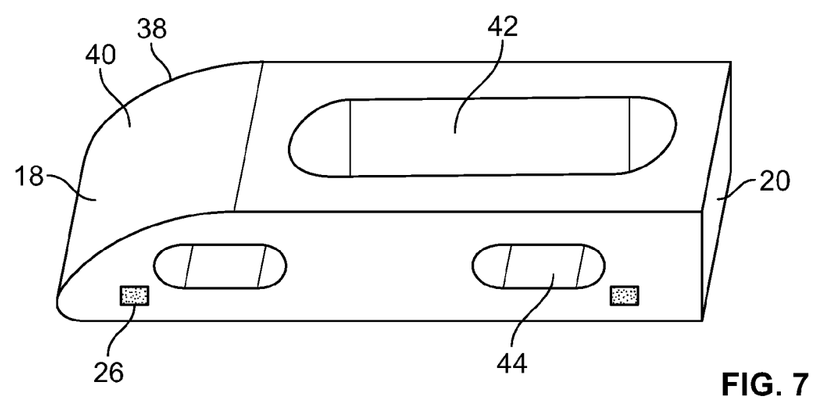
FIG. 7 is a perspective view of an alternative embodiment of the spinal implant in accordance with the present invention.
Figure 8:
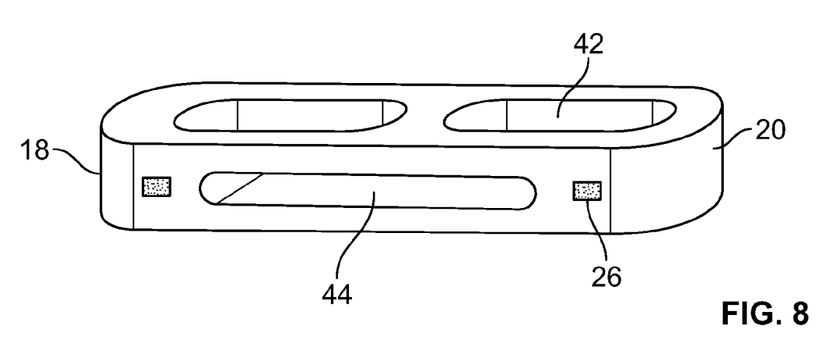
FIG. 8 is a perspective view of an alternative embodiment of the spinal implant in accordance with the present invention.
Figure 9:
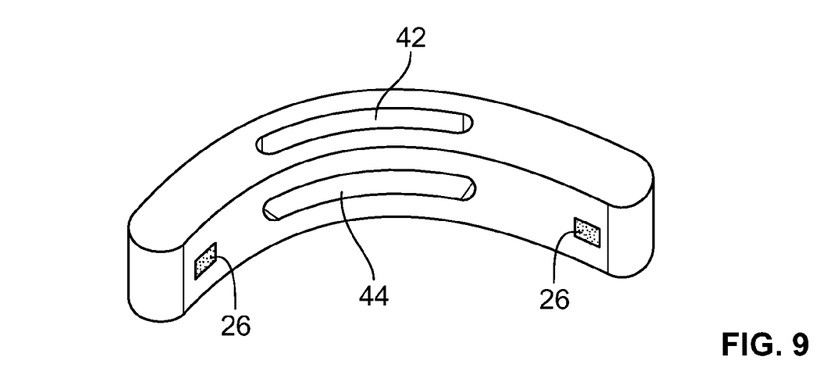
FIG. 9 is a perspective view of an alternative embodiment of the spinal implant in accordance with the present invention.

Referring back to FIGS. 7-9, alternative embodiments of the spinal implants 10 are shown. The size and shape of the spinal implant 10 can be varied depending on the type of surgical procedure undertake, the size and shape of the individual's vertebrae, the type of procedure used (for example PLIF or TLIF), or vertebral separation and/or support. The spinal implant 10 may also contain additional features that aid in implantation. For example, FIG. 7 illustrates a spinal implant 10 in which one of the opposing ends 18 contains a curved surface 38, forming an angled or ramped surface area 40. FIG. 8 illustrates a spinal implant 10 in which opposing sides 18 and 20 are curved. Referring to FIG. 9, the main body 12 is shown having a half-moon or crescent shape. Each of the embodiments shown in FIGS. 7-9, as well as those illustrated in FIGS. 1-6 may contain cancellous autograft bone, allograft bone, demineralized bone matrix (DBM), porous synthetic bone graft substitutes, bone morphogenic proteins (BMP), or combinations thereof, inserted within a hollow portion of the spinal implant 10. Additionally, the spinal implant 10 may contain one or more vertical apertures 42 and one or more traverse apertures 44 sized and shaped to maximize access to bone graft material provided within the implant 10. An additional opening (not illustrated) may be utilized to facilitate manipulation of the implant 10 by a surgical tool.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An implant comprising:
   a body having a top surface and bottom surface parallel to one another, a first sidewall and a second sidewall opposing one another, the first sidewall having a first length and the second side wall having a second length, and a third sidewall and a fourth sidewall opposing one another, the third sidewall having a third length and the fourth sidewall having a fourth length, the third length and fourth length being greater than the first length and second length, the body including one or more vertical apertures opening through at least one of the top and bottom surfaces and one or more transverse apertures opening through at least one of the third and fourth sidewalls; and
   a first magnet embedded in the third sidewall of the implant adjacent to the first sidewall and between the top surface and the bottom surface, a second magnet embedded in the third sidewall of the implant adjacent to the second sidewall and between the top surface and the bottom surface, a third magnet embedded in the fourth sidewall of the implant adjacent to the first sidewall and between the top surface and bottom surface, and a fourth magnet embedded in the fourth sidewall of the implant adjacent the second sidewall and between the top surface and bottom surface.

2. The implant of claim 1, wherein the top and bottom surfaces contain at least one of ridges and teeth.

3. The implant of claim 1, wherein the implant is made of a durable material selected from stainless steel, stainless steel alloy, titanium, aluminum, aluminum alloy, carbon fiber composite, polymeric, ceramic, composite materials, biocompatible polymer matrix reinforced with bioactive fillers and/or fibers, polyetherether-ketone (PEEK), polyvinyl chloride (PVC), polyethylene polyesters, polycarbonate, Teflon coated metal, ultra high molecular weight polyethylene (UHMWPE), and urethane dimethacrylate (DUDMA)/tri-ethylene glycol dimethacrylate (TEDGMA) blended resins with fillers and/or fibers.

4. The implant of claim 1, wherein each of the first magnet, second magnet, third magnet, and fourth magnet are one of a permanent magnet, temporary magnet, and electromagnet.

5. The implant of claim 1, wherein each of the first magnet, second magnet, third magnet, and fourth magnet is integrally formed within the implant.

6. The implant of claim 1, wherein one of the first sidewall and second sidewall is curved.

7. The implant of claim 1, wherein one of the first sidewall and second sidewall is ramped.

8. The implant of claim 1, wherein at least one of the third sidewall and fourth sidewall is curved.

9. The implant of claim 1, wherein the first, second, third, and fourth magnets are formed from one of magnetic powder and nano-magnetic particles incorporated into the implant body material.

10. The implant of claim 1, wherein the implant contains bone graft material within a hollow potion of the implant comprising the one or more vertical apertures.

11. The implant of claim 10, wherein the bone graft material comprises one or more of cancellous auto graft bone, allograft bone, demineralized bone matrix, porous synthetic bone graft substitutes, and bone morphogenic proteins.

12. A system of at least two implants comprising:
   a first implant body having a top surface and bottom surface parallel to one another, a first sidewall and a second sidewall opposing one another, the first sidewall having a first length and the second sidewall having a second length, and a third sidewall and a fourth sidewall opposing one another, the third sidewall having a third length and the fourth sidewall having a fourth length, the third length and fourth length being greater than the first length and second length, the body including one or more vertical apertures opening through at least one of the top and bottom surfaces and one or more transverse apertures opening through at least one of the third and fourth sidewalls;
   a first magnet embedded in the third sidewall of the implant adjacent to the first sidewall and between the top surface and the bottom surface, a second magnet embedded in the third sidewall of the implant adjacent to the second sidewall and between the top surface and the bottom surface, a third magnet embedded in the fourth sidewall of the implant adjacent to the first sidewall and between the top surface and bottom surface, and a fourth magnet embedded in the fourth sidewall of the implant adjacent the second sidewall and between the top surface and bottom surface, wherein at least of the first, second, third, and fourth magnets magnetically effect at least two magnets of a second implant like-configured to the first implant.

13. The system of claim 12, wherein the magnetic effect is to draw the at least two implants together.

14. The system of claim 12, wherein the magnetic effect is to repel the at least two implants apart.

15. A method for performing surgery comprising:
   inserting a first implant into a prepared disc space, the firm implant comprising a body having a top surface and a bottom surface parallel to one another, a first sidewall and a second sidewall opposing one another, the first sidewall having a first length and the second sidewall having a second length, a third sidewall and a fourth sidewall opposing one another, the third sidewall having a third length and the fourth sidewall having a fourth length, the third length and the fourth length being greater than the first length and the second length, the body including one or more vertical apertures opening through at least one of the top and bottom surfaces and one or more transverse apertures opening through at least one of the third and fourth sidewalls, and a first magnet embedded in the third sidewall of the implant adjacent to the first sidewall and between the top surface and the bottom surface, a second magnet embedded in the third sidewall of the implant adjacent to the second sidewall and between the top surface and the bottom surface, a third magnet embedded in the fourth sidewall of the implant adjacent to the first sidewall and between the top surface and the bottom surface, and a fourth magnet embedded in the fourth sidewall of the implant adjacent the second sidewall and between the top surface and the bottom surface;
   inserting a second implant like-configured to the first implant into the prepared disc space in proximity of the first implant;
   wherein a magnetic field is created by at least two of the first, second, third, and fourth magnets of the first implant and at least two magnets of the second implant to draw the first implant and the second implant into self-alignment without surgeon manipulation.

\* \* \* \* \*